United States Patent [19]  [11] 4,332,721
Bernini  [45] Jun. 1, 1982

[54] PROCESS FOR PREPARING MICRONIZED SPIRONOLACTONE

[75] Inventor: Giuseppe Bernini, Milan, Italy

[73] Assignee: Secrifarma S.p.A., Milan, Italy

[21] Appl. No.: 235,816

[22] Filed: Feb. 19, 1981

[30] Foreign Application Priority Data

Mar. 6, 1980 [IT] Italy ................................ 20391 A/80

[51] Int. Cl.³ ............................................. C07J 19/00
[52] U.S. Cl. ................................................. 260/239.57
[58] Field of Search ..................................... 260/239.57

[56] References Cited

U.S. PATENT DOCUMENTS 3,897,417  7/1975  Warnaut et al. ................. 260/239.57

*Primary Examiner*—Elbert L. Roberts
*Attorney, Agent, or Firm*—Ladas & Parry

[57] ABSTRACT

The invention relates to a process for preparing a spironolactone, having increased biological activity, by precipitation with water from a solution with preferably organic solvents at a temperature between 0° and 30° C. and under vigorous stirring.

3 Claims, No Drawings

PROCESS FOR PREPARING MICRONIZED SPIRONOLACTONE

DESCRIPTION

The present invention relates to a process for preparing a micronized spironolactone having increased biological activity.

As known, spironolactone, i.e. pregn-4-ene-21-carboxylic acid, 7-aceytlthio)-17-hydroxy-3-oxo-, γ-lactone, (7α, 17α)- of the formula

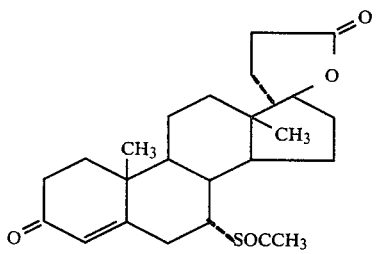

is widely used in human and veterinary therapy due to its anti-aldosteronic and diuretic activity.

It is also well known that the biological activity of said compound is connected to the size of the crystals thereof, and that the micronized form is several times more active than the non-micronized form (see Dideberg, Du Pont, in Acta Crystallogr. Sect. B 28, 3014 (1972) and Bauer and coll. in Armeimittel-Forsch. 12, 487 (1962)).

The processes used to micronize spironolactone are generally mechanical (jet mill) and the size of the crystals is usually from 2 to 5 microns.

It is further known that spironolactone can exist as a number of polymorphic forms depending on the way in which it is crystallized (Sutter, J. L. and Lan, E. P. K. Analytical profile at drug substance, Vol. 4, page 431).

It has now been found that it is possible to obtain increased biological activity, to be more exact, higher hematic levels, when spironolactone is micronized by precipitation with water from a solution in solvents, preferably organic in nature. In this way, the size of the crystals is still from 2 to 5 microns, but the X-ray diffraction pattern is characteristic and different from that obtained by means of mechanical micronization.

In order to solubilize the spironolactone, different solvents, such as lower alcohols, ethers, ketones, ether-alcohols, glycols and so on, may be used.

In particular, one can use methanol, ethanol, isopropanol, tetrahydrofuran, dioxane, acetone, ethyl- or methyl-cellosolve, ethylene glycol and so on.

Generally, it is preferable that the used solvent be water-soluble at any ratio.

The temperature at which precipitation is performed must preferably be from 0° to 30° C., and stirring must be very vigorous so as not to permit an increase in crystal size.

Also the solvent-water ratio must be contemplated, through it can vary broadly. For convenience reasons, it can be comprised from 1÷10 to 1÷100.

The following Example shall clarify the present invention, without, however, limiting its scope in any way.

EXAMPLE

10 Kg of spironolactone, solubilized in 50 Kg of acetone, are poured into 500 liters of water under a good stirring. The precipitate of micronized spironolactone is collected and dried.

Yield: nearly quantitative.

The product obtained shows an X-ray diffraction pattern as specified in the following Table.

TABLE

X-RAY DIFFRACTION PATTERN
Spironolactone

| d(A) | $I/I_o$ |
|------|---------|
| 13.70 | 6 |
| 10.46 | 35 |
| 8.67 | 100 |
| 7.37 | 4 |
| 7.09 | 5 |
| 6.94 | 5 |
| 6.68 | 4 |
| 6.44 | 3 |
| 6.32 | 11 |
| 5.83 | 3 |
| 5.64 | 13 |
| 5.47 | 83 |
| 5.31 | 72 |
| 5.22 | 15 |
| 4.86 | 23 |
| 4.68 | 34 |
| 4.60 | 19 |
| 4.13 | 4 |
| 4.03 | 8 |
| 3.91 | 19 |
| 3.75 | 5 |
| 3.66 | 23 |
| 3.47 | 6 |
| 3.39 | 6 |
| 3.27 | 6 |
| 2.98 | 6 |

I claim:

1. A process for preparing micronized spironolactone having increased biological activity, which comprises micronizing the spironolactone by precipitation with water from a solution with preferably organic solvents selected from the group consisting of lower alcohols, ethers, lactones, ether-alcohols and glycols at a temperature from 0° to 30° C. and under vigorous stirring.

2. Process for preparing micronized spironolactone according to claim 1, wherein methanol, ethanol, isopropanol, tetrahydrofuran, acetone, dioxane, ethylene glycol, methyl- or ethyl-cellosolve is employed as the organic solvent.

3. A process for preparing micronized spironolactone having increased biological activity, which comprises micronizing the spironolactone by precipitation with water from a solution with preferably organic solvents selected from the group consisting of lower alcohols, ethers, ketones ether-alcohols and glycols at a temperature from 0° to 30° C. and under vigorous stirring.

* * * * *